United States Patent
Park (10) Patent No.: US 9,687,690 B2
(45) Date of Patent: Jun. 27, 2017

(54) CUSTOMIZED EXERCISE SYSTEM AND CUSTOMIZED EXERCISE METHOD

(71) Applicant: IFIVE CO., LTD., Seongnam-si, Gyeonggi-do (KR)

(72) Inventor: Chul Woong Park, Yongin-si (KR)

(73) Assignee: IFIVE CO., LTD., Seongnam-si, Gyeonggi-Do (KR)

( * ) Notice: Subject to any disclaimer, the term of this patent is extended or adjusted under 35 U.S.C. 154(b) by 0 days.

(21) Appl. No.: 14/751,010

(22) Filed: Jun. 25, 2015

(65) Prior Publication Data

US 2015/0375039 A1     Dec. 31, 2015

(30) Foreign Application Priority Data

Jun. 26, 2014  (KR) .................. 10-2014-0079112

(51) Int. Cl.
*A63B 71/00* (2006.01)
*A63B 21/072* (2006.01)
(Continued)

(52) U.S. Cl.
CPC ...... *A63B 21/0726* (2013.01); *A63B 23/1209* (2013.01); *G06F 19/3481* (2013.01); *G06K 9/00342* (2013.01); *A63B 23/0494* (2013.01); *A63B 2071/065* (2013.01); *A63B 2220/10* (2013.01); *A63B 2220/16* (2013.01); *A63B 2220/40* (2013.01); *A63B 2225/50* (2013.01); *H04M 1/7253* (2013.01)

(58) Field of Classification Search
CPC ... A63B 21/072–21/0783; A63B 21/08; A63B 24/0003; A63B 24/0006; A63B 24/0021; A63B 24/0062; A63B 24/0075; A63B 2024/0009; A63B 2024/0015; A63B 2024/0056; A63B 2024/0065; A63B 2024/0068; A63B 2024/0071
USPC ....................... 482/1, 8, 9, 92–109
See application file for complete search history.

(56) References Cited

U.S. PATENT DOCUMENTS 8,608,595 B2 * 12/2013 Ikka .................. A63B 69/3685
                                                    473/219
8,718,938 B2 *  5/2014 Wolf .................... G01C 21/16
                                                    33/355 R
(Continued)

FOREIGN PATENT DOCUMENTS

KR    10-2005-011217    11/2005
KR    10-20130100816     9/2013
(Continued)

OTHER PUBLICATIONS

Korea Office Action for 10-2014-0079112 dated Sep. 5, 2014.

*Primary Examiner* — Stephen R Crow
*Assistant Examiner* — Garrett Atkinson
(74) *Attorney, Agent, or Firm* — Koppel, Patrick, Heybl & Philpott (57) ABSTRACT

Provided is a customized exercise system including exercise equipment comprising a sensor, a server storing information about an exercise method and an exercise amount corresponding to a body condition, and a mobile terminal receiving information about an exercise method and an exercise amount that are suitable for a user from the server and providing the transmitted information to the exercise equipment, in which a body condition of an individual user is determined using the sensor.

14 Claims, 8 Drawing Sheets

(51) Int. Cl.
*A63B 21/075* (2006.01)
*A63B 23/12* (2006.01)
*G06F 19/00* (2011.01)
*G06K 9/00* (2006.01)
A63B 23/04 (2006.01)
A63B 71/06 (2006.01)
H04M 1/725 (2006.01)

(56) References Cited

U.S. PATENT DOCUMENTS

| | | | | |
|---|---|---|---|---|
| 8,725,452 | B2* | 5/2014 | Han | A61B 5/11 |
| | | | | 702/152 |
| 8,781,610 | B2* | 7/2014 | Han | A63B 69/3623 |
| | | | | 463/20 |
| 2012/0000300 | A1* | 1/2012 | Sunagawa | A61B 5/1116 |
| | | | | 73/865.4 |
| 2012/0278023 | A1* | 11/2012 | Han | G01C 21/165 |
| | | | | 702/87 |
| 2012/0317064 | A1* | 12/2012 | Hagiwara | A63B 24/0075 |
| | | | | 706/46 |
| 2013/0090212 | A1* | 4/2013 | Wang | A63B 71/0619 |
| | | | | 482/8 |
| 2013/0310711 | A1* | 11/2013 | Wang | A61B 5/1121 |
| | | | | 600/595 |
| 2014/0081182 | A1* | 3/2014 | Klose | A61B 5/0002 |
| | | | | 600/595 |
| 2014/0114453 | A1* | 4/2014 | Bentley | A61B 5/1122 |
| | | | | 700/91 |
| 2014/0278218 | A1* | 9/2014 | Chang | G01P 15/00 |
| | | | | 702/150 |
| 2014/0342844 | A1* | 11/2014 | Mooney | G06K 9/00342 |
| | | | | 473/266 |
| 2014/0368424 | A1* | 12/2014 | Choi | G06F 3/015 |
| | | | | 345/156 |
| 2015/0081057 | A1* | 3/2015 | Hamada | A63B 23/12 |
| | | | | 700/91 |
| 2015/0148594 | A1* | 5/2015 | Tadano | A61B 1/00149 |
| | | | | 600/102 |
| 2015/0229888 | A1* | 8/2015 | Harada | G06K 9/00664 |
| | | | | 348/207.1 |

FOREIGN PATENT DOCUMENTS

WO WO 2006/001602 A1 1/2006
WO WO 2013/115432 A1 8/2013

\* cited by examiner

CUSTOMIZED EXERCISE SYSTEM AND CUSTOMIZED EXERCISE METHOD

CROSS-REFERENCE TO RELATED APPLICATION

This application claims the benefit of Korean Patent Application No. 10-2014-0079112, filed on Jun. 26, 2014, in the Korean Intellectual Property Office, the disclosure of which is incorporated herein in its entirety by reference.

BACKGROUND

1. Field

One or more exemplary embodiments relate to a customized exercise system and a customized exercise method.

2. Description of the Related Art

As the amount of people lacking exercise is on the rapid rise in the modern society, the frequency of occurrence of diseases such as obesity, high blood pressure, and so forth is steadily increasing. Thus, more and more people exercise for physical strength and health at home or fitness centers.

In spite of different body conditions from people to people, people exercise by the same exercise method and the same exercise amount by using the same exercise facility. In this case, even if people exercise, exercise efficiency may be low or one's health may be damaged by immoderate exercise.

Moreover, it is very cumbersome for people to record the amount of exercise after exercising, and also, people may not be able to remember the amount of exercise they did. Thus, people may neglect the recording, which may make it difficult for people to check the amount of exercise they did, an exercise method, and so forth.

SUMMARY

One or more exemplary embodiments include a customized exercise system and a customized exercise method.

Additional aspects will be set forth in part in the description which follows and, in part, will be apparent from the description, or may be learned by practice of the presented embodiments.

According to one or more exemplary embodiments, a customized exercise system includes exercise equipment including a sensor, a server storing information about an exercise method and an exercise amount corresponding to a body condition, and a mobile terminal receiving information about an exercise method and an exercise amount that are suitable for a user from the server and providing the transmitted information to the exercise equipment, in which a body condition of an individual user is determined using the sensor.

In the current embodiment, the exercise equipment may include a memory that stores information, and the memory stores a predetermined posture required for measurement of a body condition of a user, information about an exercise method and an exercise amount that are suitable for the user, and information about an exercise amount of exercise that the user actually does.

In the current embodiment, as the user holds the predetermined posture stored in the memory and requested from the user, a body condition of the individual user may be measured by the sensor.

In the current embodiment, the body condition of the user, determined using the sensor, may include a length of an arm of the user and a pivoting angle of the arm of the user.

In the current embodiment, the body condition of the user determined using the sensor may include a length of a leg of the user.

In the current embodiment, the sensor may include a geomagnetic sensor.

In the current embodiment, the sensor may include an acceleration sensor.

In the current embodiment, the sensor may include a gyro sensor.

In the current embodiment, the exercise equipment may include a display unit that displays information about a measured exercise amount.

According to one or more exemplary embodiments, a customized exercise method includes a body condition measuring operation of measuring a body condition of a user by using a sensor included in exercise equipment, an information extraction operation of extracting an exercise method and an exercise amount that correspond to an analyzed body condition from information stored in a server, and an information transmission operation of transmitting information about an exercise method and an exercise amount that are suitable for a user from the server to a mobile terminal and/or the exercise equipment of the user.

In the current embodiment, the exercise equipment may include a memory that stores information, and the memory stores a predetermined posture required for measurement of a body condition of a user, information about an exercise method and an exercise amount that are suitable for the user, and information about an exercise amount of exercise that the user actually does.

In the current embodiment, the customized exercise method may further include a posture suggestion operation of suggesting a predetermined posture stored in the memory to the mobile terminal for measurement of a body condition of a user, before performing the body condition measuring operation.

In the current embodiment, the body condition analyzing operation may include analyzing a body condition of a user by using a pivoting angle and acceleration that are sensed by the sensor in the posture suggestion operation.

The body condition may include a length of an arm of the user and a pivoting angle of the arm of the user.

The body condition may include a length of a leg of the user.

The customized exercise method may further include an information storing operation of storing information about an exercise method and an exercise amount of exercise that the user actually does in a mobile terminal and/or a server, after performing the information transmission operation.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items.

Various changes may be made to the inventive concept and the inventive concept may have various embodiments which will be described in detail with reference to the drawings. However, the embodiments according to the concept of the inventive concept are not construed as limited to specified disclosures, and include all changes, equivalents, or substitutes that do not depart from the spirit and technical scope of the inventive concept. Throughout the drawings, like reference numerals refer to like components even though the components are illustrated in different drawings.

Although the terms such as "first" and "second" used in the various exemplary embodiments of the inventive concept may modify various elements of the various exemplary embodiments, these terms do not limit the corresponding elements.

The terms used in the various exemplary embodiments of the inventive concept are for the purpose of describing particular exemplary embodiments only and are not intended to be limiting. The term "include" or "may include" used in the exemplary embodiments of the inventive concept indicates the presence of disclosed corresponding functions, operations, elements, or the like, and does not limit additional one or more functions, operations, elements, or the like. In addition, it should be understood that the term "include" or "has" used in the exemplary embodiments of the inventive concept is to indicate the presence of features, numbers, steps, operations, elements, parts, or a combination thereof described in the specifications, and does not preclude the presence or addition of one or more other features, numbers, steps, operations, elements, parts, or a combination thereof.

Hereinafter, embodiments of the inventive concept will be described in detail with reference to the accompanying drawings.

Figure 1:
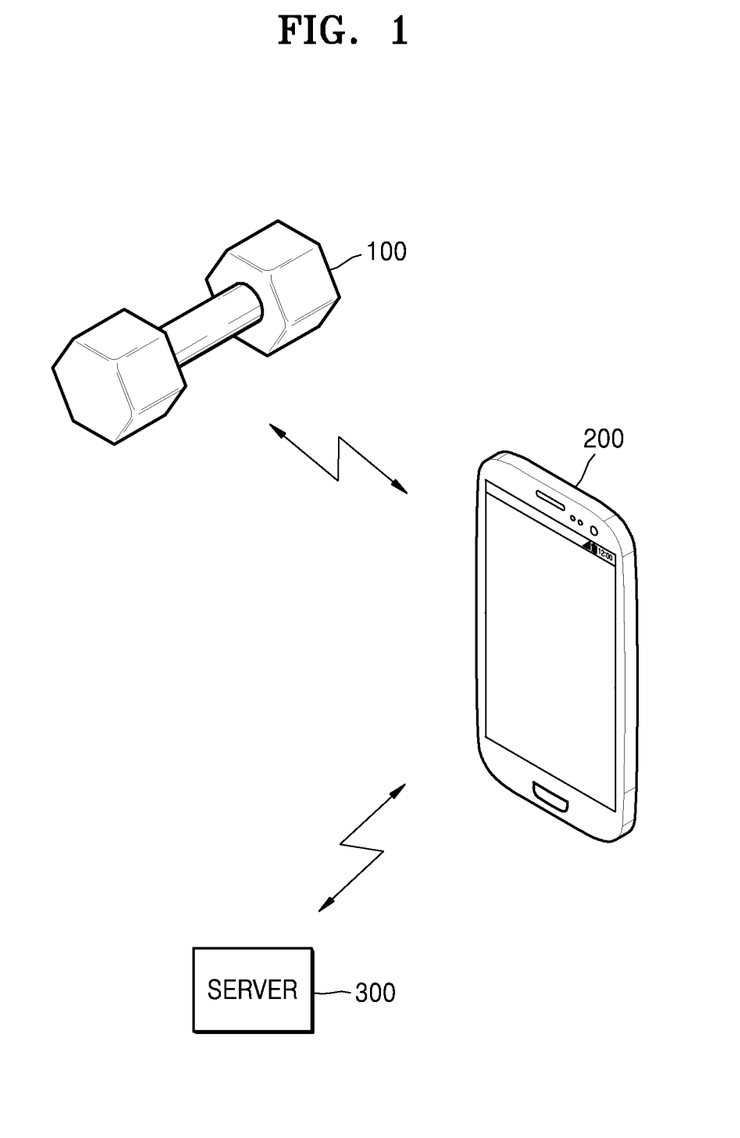
FIG. 1 schematically illustrates a customized exercise system according to an embodiment of the inventive concept.

FIG. 1 schematically illustrates a customized exercise system according to an embodiment of the inventive concept. However, the customized exercise system illustrated in FIG. 1 is merely an example and the inventive concept is not limited thereto.

As illustrated in FIG. 1, the customized exercise system according to an embodiment of the inventive concept may include exercise equipment 100, a mobile terminal 200, and a server 300.

The exercise equipment 100 may be a set of dumbbells as illustrated in FIG. 1, but may also include any equipment that a user uses to exercise.

The exercise equipment 100 may include a sensor (not illustrated). The sensor measures acceleration, a pivoting angle, and a position of the exercise equipment 100 when the exercise equipment 100 moves. However, an exercise value that may be sensed by the sensor is not limited to these values.

As the sensor measures an exercise value, such as acceleration, a pivoting angle, and a position, upon movement of the exercise equipment 100, a body condition of an individual user may be measured. Once the body condition of the individual user is determined using the sensor, customized exercise for the user's body condition may be done.

That is, for typically used exercise equipment, even if body conditions differ from user to user, most users use the exercise equipment with the same exercise posture and the same exercise method. On the other hand, using the customized exercise system according to the current embodiment of the inventive concept, a body condition of an individual user is determined through the sensor before the user exercises because body conditions differ from user to user, thereby allowing the user to exercise in a customized fashion.

A way to determine a body condition of an individual user using the sensor will be described later in more detail.

The customized exercise system according to the current embodiment of the inventive concept may include the server 300.

The server 300 may store information about an exercise method and the amount of exercise which correspond to a body condition. Depending on a body condition of an individual user, a suitable exercise method, an exercise posture, and an exercise amount may vary. Therefore, it may be desirable to provide an exercise method, an exercise posture, and an exercise amount that are suitable for a body condition of an individual user using the exercise equipment 100.

Thus, the server 300 stores data corresponding to a body condition, and the data may include an exercise method, an exercise posture, and an exercise amount. Information about exercise provided to a user may also be included in the data, without being limited to the above examples.

Once a body condition of an individual user is determined using the sensor, information about an exercise method, an exercise posture, and an exercise amount, stored in the server 300, as being suitable for the measured body condition may be extracted.

The customized exercise system according to the current embodiment of the inventive concept may include the mobile terminal 200. The mobile terminal 200 may be, but not limited to, a cellular phone, as illustrated in FIG. 1, and may include any portable device including a display, such as a tablet Personal Computer (PC).

Once the body condition of the individual user is determined using the sensor and the information about the exercise method, the exercise posture, and the exercise amount, suitable for the determined body condition, is extracted, the information may be transmitted to the mobile terminal 200.

The user may recognize the transmitted information through the display of the mobile terminal 200.

That is, if the exercise posture, the exercise method, and the exercise amount suitable for the body condition of the individual user are transmitted from the server 300 to the mobile terminal 200, the user may recognize the information transmitted to the mobile terminal 200 and refers to the transmitted information when exercising with the exercise equipment 100.

The exercise equipment 100 may further include a memory (not shown) storing information.

The memory may store information commonly provided to any user at first and information about individual users.

The information commonly provided to any user at first is information about a posture required for determining a body condition of an individual user, as described together in detail with a method of determining a body condition of an individual user using the sensor.

The memory also stores the information about an exercise method, an exercise posture, and an exercise amount that are suitable for an individual user. The information about an exercise method, an exercise posture, and an exercise amount that are suitable for an individual user may be transmitted to the exercise equipment 100 as well as to the mobile terminal 200 from the server 300.

In this case, the information about exercise suitable for an individual user is stored in the exercise equipment 100, allowing the user to exercise in a customized fashion.

The memory may also store information about the exercise the user has done.

When exercising based on the provided information about suitable exercise, the user may exercise based on the provided information or may flexibly exercise by changing an exercise posture, an exercise amount, and so forth.

Therefore, when the user exercises, information about an exercise posture or an exercise amount of exercise that the user actually does may be determined by the exercise equipment 100 and stored in the memory of the exercise equipment 100.

The information stored in the memory may be transmitted to and stored in the mobile terminal 200 or the server 300 through communication with the mobile terminal 200 or the server 300.

If the information about exercise done by the user is stored in the mobile terminal 200 or the server 300 as information for an individual user, an achievement of the exercise of the user may be recognized and the information may be referred to for future exercise.

In the customized exercise system according to the current embodiment, a body condition of an individual user may be determined using the sensor as described below.

As described above, the memory may store the information about the posture, which is commonly provided to any user at first. That is, if the user is requested to hold a predetermined posture and holds that posture, a body condition of the user may be measured by the sensor included in the exercise equipment 100.

The posture requested from the user may be directly displayed on the exercise equipment 100 and the user may recognize the posture if the exercise equipment 100 includes the display unit, or the requested posture may be transmitted from the exercise equipment 100 to the mobile terminal 200 through communication between the exercise equipment 100 and the mobile terminal 200 and the user may recognize the posture through the mobile terminal 200.

Figure 2:
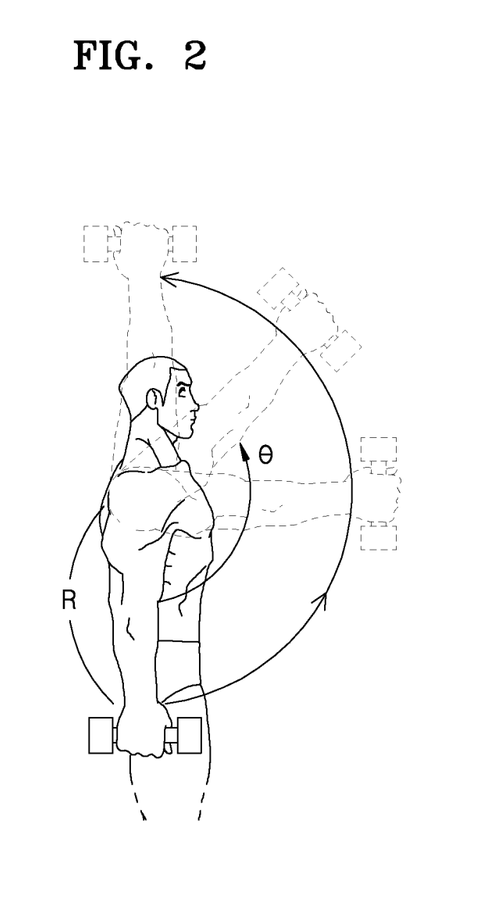
FIG. 2 illustrates a state where a user pivots an arm, holding exercise equipment in a hand.

FIGS. 2 through 5 schematically illustrate a method of measuring a body condition of a user. FIG. 2 schematically illustrates a state where the user pivots an arm, while holding the exercise equipment 100 in one hand. Thus, a pivoting angle θ and a length R of the arm of the user are measured by the sensor included in the exercise equipment 100.

Once the user pivots the arm, while holding the exercise equipment 100 in one hand, the pivoting angle θ of the arm of the user, a time t taken for movement of the arm, and an acceleration a of movement of the arm are sensed by the sensor included in the exercise equipment 100. Values sensed by the sensor are not limited to these values, and may also include other values for recognizing the body condition of the user.

According to an embodiment of the inventive concept, when the user pivots the exercise equipment 100, while holding the exercise equipment 100, for a predetermined time, once the time t taken for movement of the arm and the acceleration a are sensed, a velocity v of movement of the arm may be calculated as follows:

$$v = \int a \, dt$$

By using the velocity v of movement of the arm and the time t taken for movement of the arm, a distance s of movement of the arm may be calculated as follows:

$$s = \int v \, dt$$

By using the distance s of movement of the arm, calculated in this way, and the sensed pivoting angle θ of the arm, the length R of the arm of the user may be calculated as follows:

$$2\pi R \theta = \pi R s$$

$$s = R \theta$$

$$R = s/\theta$$

That is, the pivoting angle θ of the arm of the user, the time t taken for movement of the arm, and the acceleration a may be sensed using the sensor included in the exercise equipment 100, and the length R of the arm of the user may be finally calculated using these sensed values.

Figure 3:
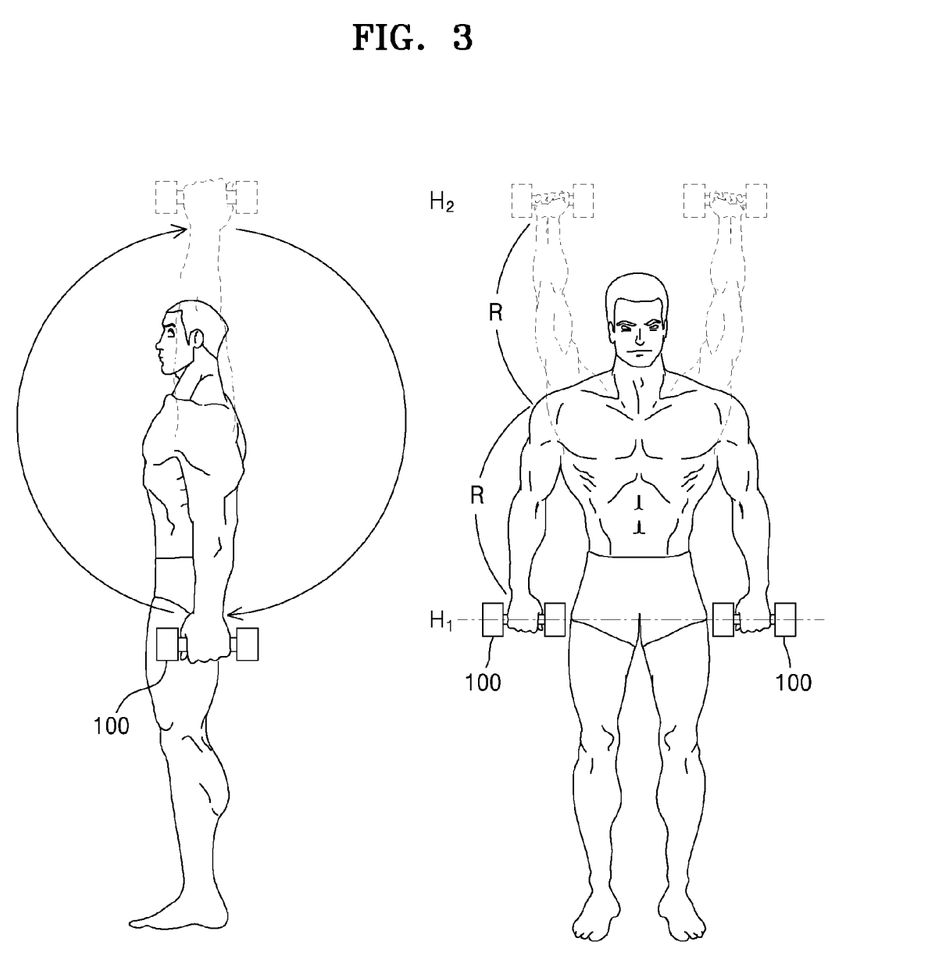
FIG. 3 illustrates a state where a user raises and lowers the arms, holding exercise equipment in both hands.

FIG. 3 illustrates a state where the user raises and lowers the arms, while holding the exercise equipment 100 in both hands.

Although the pivoting angle θ of the arm and the length R of the arm may be measured by the pivoting of the arm, as described with reference to FIG. 2, the length R of the arm may also be measured by the user's raising and lowering of the arms, as illustrated in FIG. 3.

In this case, like when the user pivots the arm, as an action of raising and lowering arms, stored in the memory of the exercise equipment 100, is displayed on the exercise equipment 100 or the mobile terminal 200, the user may be requested to hold a predetermined posture.

When the user does the action stored in the memory and then is requested, that is, to do the action of raising and then lowering the arms, while holding the exercise equipment 100 in both hands, the length R of the arm may be sensed by the sensor included in the exercise equipment 100.

If the user lets the arms down, while holding the exercise equipment 100 in both hands, and then stretches the arms over the head, as illustrated in FIG. 3, then the sensor senses a lowest position $H_1$ and a highest position $H_2$.

A difference between the lowest position $H_1$ and the highest position $H_2$ may be two times the length R of the arm of the user, as illustrated in FIG. 3.

Thus, the length R of the arm of the user may be determined using the sensor, and the length R of the arm of the user may be stored in the memory of the exercise equipment 100 and may also be transmitted to the mobile terminal 200 and/or the server 300.

Figure 4:
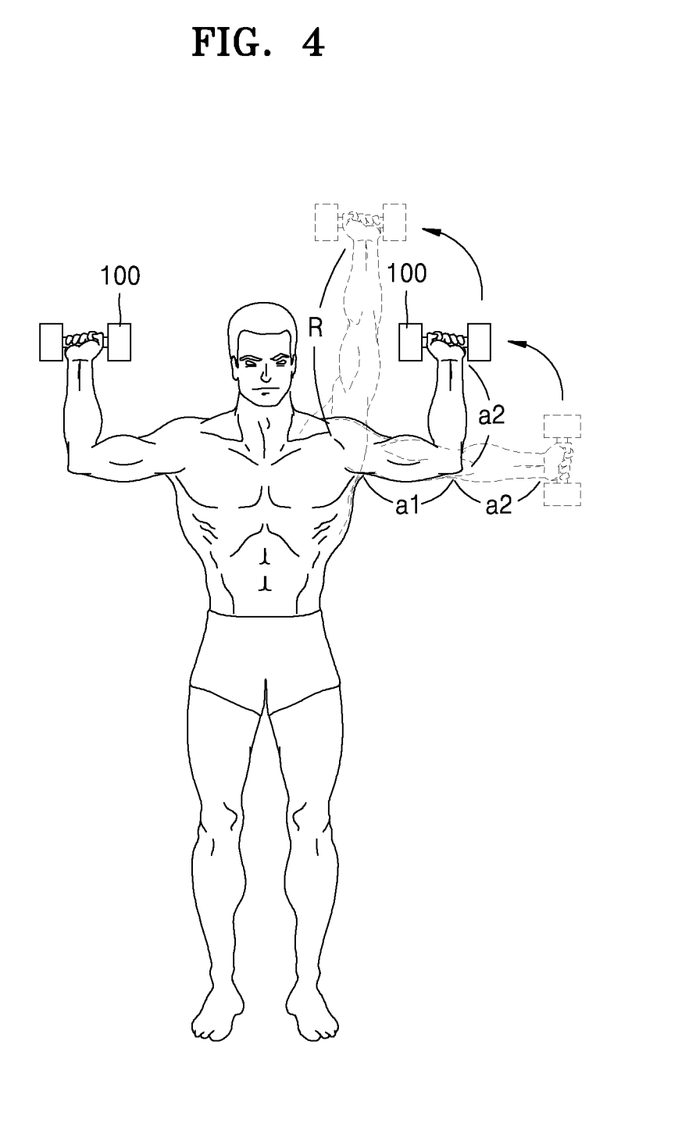
FIG. 4 illustrates a state where a user bends, stretches, and then raises the elbows.

FIG. 4 illustrates a state where the user holds the exercise equipment 100, by bending the arms. To provide a more suitable exercise method, exercise posture, and exercise amount to the user, the user's body condition may be more accurately determined.

As illustrated in FIG. 4, the total length R of the arm may be divided into a length a1 from the shoulder to the elbow and a length a2 from the elbow to the hand.

As the length R of the arm, the length a1 from the shoulder to the elbow, and the length a2 from the elbow to the hand differ from user to user, a more suitable exercise posture and exercise amount may be provided to the user by recognizing detailed lengths.

The partial lengths a1 and a2 of the length R of the arm of the user may be measured using the sensor included in the exercise equipment 100 in various ways.

FIG. 4 shows an example of measurement of the length a1 from the shoulder to the elbow and the length a2 from the elbow to the hand.

First, as described before, the predetermined posture stored in the memory may be requested from the user, and the user may then hold that posture.

As illustrated in FIG. 4, while holding the exercise equipment 100 in both hands, the user extends both arms to the sides and perpendicularly bends the elbows with the exercise equipment 100 facing the sky. By doing this action, the sensor included in the exercise equipment 100 senses a position at the shoulder height and then senses a position higher by the length a2 from the elbow to the hand. That is, the length a2 from the elbow to the hand may be measured as a height difference between the two positions.

The user may raise the arm over the head from the posture of perpendicularly bending the elbows and holding the exercise equipment 100 facing the sky, as illustrated in FIG. 4. By doing this action, the exercise equipment 100 is positioned away from the body by the length a1 from the shoulder to the elbow, and then is positioned directly above the shoulder, such that the sensor senses the position and recognizes the length a1 from the shoulder to the elbow.

Because a1+a2=R, once the length a2 from the elbow to the hand is measured after the length R of the arm is recognized in advance, the length a1 from the shoulder to the elbow may be obtained by subtracting the length a2 from the elbow to the hand from the length R of the arm (R−a1=a2).

The foregoing method is merely an example for recognizing a user's detailed body condition, and the inventive concept is not limited to this method and may include any method of recognizing the length R of the arm of the user, the length a1 from the shoulder to the elbow, and the length a2 from the elbow to the hand.

That is, the customized exercise system according to the current embodiment may request the user to hold a predetermined posture stored in the memory before the user uses the exercise equipment 100 first.

The predetermined posture requested from the user may be the above-described action such as pivoting the arm or simply raising and lowering the arm. The predetermined posture may include any action for recognizing the user's body condition by the user doing an action, without being limited to the above example.

As such, the particular posture requested from the user may be displayed on the exercise equipment 100 or may be transmitted to and displayed on the mobile terminal 200. If the user holds the predetermined posture requested by the exercise equipment 100 or the mobile terminal 200, information about the length R of the arm of the user, the pivoting angle θ of the arm, and so forth may be determined by the sensor.

Moreover, once the user holds the requested predetermined posture, the information about the partial length a1 from the shoulder to the elbow and the partial length a2 from the elbow to the hand, which correspond to a detailed body condition, may also be recognized.

The obtained information may be stored in the memory of the exercise equipment 100, the mobile terminal 200, or the server 300.

Figure 5:
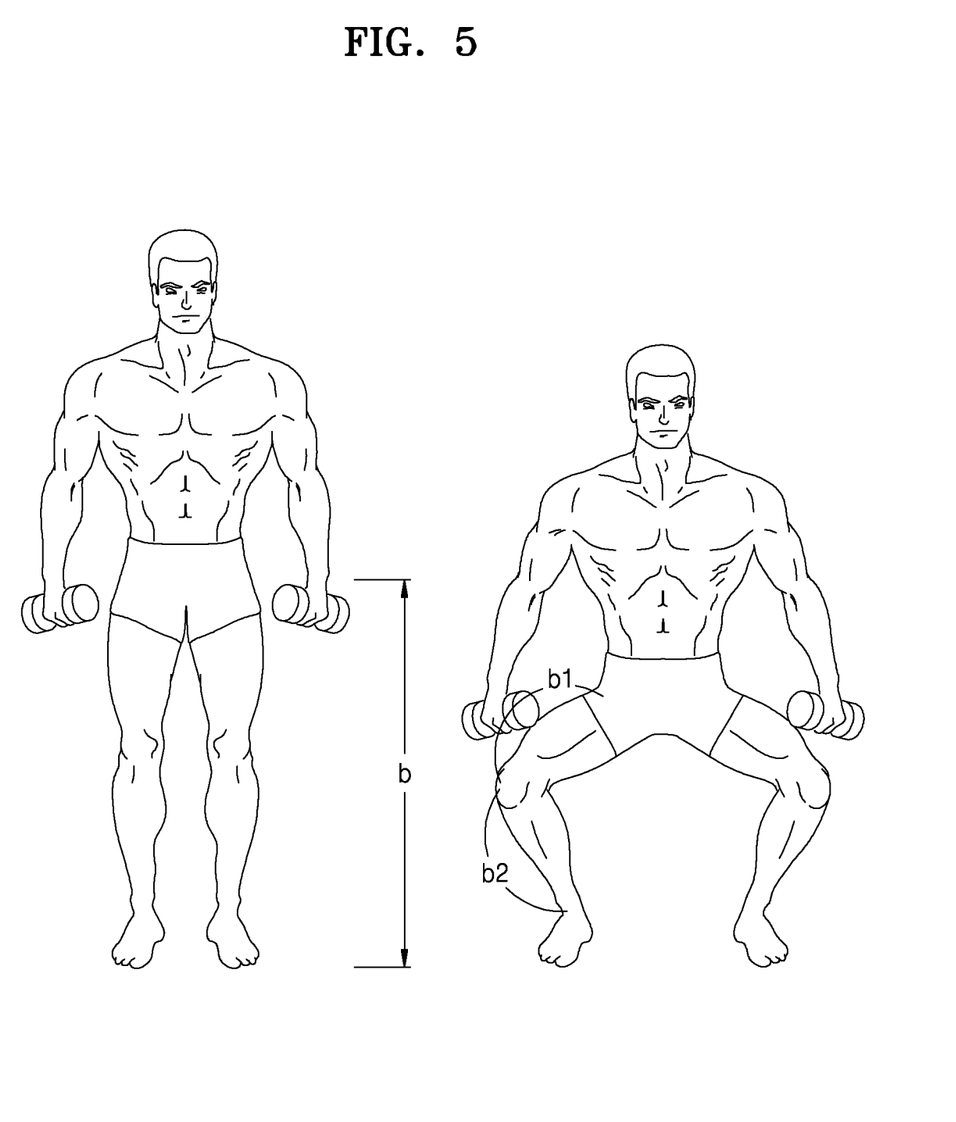
FIG. 5 illustrates a state where a user bends the knees to sit down and then stands up, holding exercise equipment in both hands.

FIG. 5 illustrates a state where a user bends the knees to sit down and then stands up, while holding the exercise equipment 100 in both hands.

As the user sits down and then stands up, while holding the exercise equipment 100 in both hands, a length b of the legs of the user, specifically, a length b1 from the waist to the knee and a length b2 from the knee to the foot may be measured.

To measure the length b of the leg, the user may do an action, while holding the exercise equipment 100 in both hands, as requested by the memory. However, any method of measuring a length of a leg may be performed and the following method is merely an example without limiting the scope of the inventive concept.

When the user holds the exercise equipment 100 and thus the exercise equipment 100 is at the waist position, the sensor may sense a position from the ground to measure the length b of the leg of the user. If the user bends the knees to move the exercise equipment 100 to the knee position and then spreads the knees to lift the exercise equipment 100 to the waist position, the exercise equipment 100 may sense a highest position and a lowest position to measure the length b1 from the waist to the knee. As illustrated in FIG. 5, because b=b1+b2, if the length b of the leg and the length b1 from the waist to the knee are determined, the length b2 from the knee to the foot may also be easily determined.

In another way, if the user slightly bends the knees to move the exercise equipment 100 to the knee position, then completely bends the knees to move the exercise equipment 100 to contact the ground, and then slightly spreads the knees to move the exercise equipment 100 to the knee position, then the highest position and the lowest position may be sensed and the length b2 from the knee to the foot may be measured.

Like when the length of the arm is measured, a predetermined posture stored in the memory is requested from the user and if the user holds the requested predetermined posture, the length b of the leg, the length b1 from the waist to the knee, and the length b2 from the knee to the foot may be measured.

Thus, the obtained information may be stored in the memory included in the exercise device 100 and may be transmitted to and stored in the mobile terminal 200 and/or the server 300.

The sensor included in the exercise equipment 100 may include a sensor for sensing a position, a sensor for sensing acceleration, a sensor for sensing a time, a sensor for sensing a moving distance, and so forth. However, any sensor for recognizing a user's body condition may also be included in the exercise equipment 100.

More specifically, the sensor may include a geomagnetic sensor used to sense a direction and a position. The sensor may also include acceleration sensor used to measure acceleration necessary for measuring a length of an arm based on pivoting of the exercise equipment 100. The sensor may also include a gyro sensor used to measure a pivoting angle, a position, and a direction of an arm based on pivoting of the exercise equipment 100.

That is, the exercise equipment 100 of the customized exercise system according to the current embodiment may also include a sensor. The sensor is a sensor for sensing information such as a position, acceleration, a pivoting angle, a direction, and so forth to recognize a user's body condition. More specifically, a geomagnetic sensor, acceleration sensor, a gyro sensor, and so forth may be included, and any sensor used to recognize the user's body condition may be included without being limited to these examples.

Thus, the user may measure the body condition in advance by taking a requested predetermined posture, while holding the exercise equipment 100 including the sensor in a hand, before starting exercise using the exercise equipment 100. As such, by measuring in advance the length R of the arm and the length b of the leg of an individual user, more specifically, the length a1 from the shoulder to the elbow, the length a2 from the elbow to the hand, the length b1 from the waist to the knee, and the length b2 from the knee to the foot, the exercise method, the exercise posture, and the amount of exercise, which are suitable for a body condition of the individual user, may be provided, allowing the user to efficiently use the exercise equipment 100 and thus providing user convenience.

As such, once the user's body condition is recognized and the information is transmitted to the server 300, the exercise method, the exercise posture, and the exercise amount that are suitable for the user's body condition, stored in the server 300, are extracted from a database, and the extracted data may be transmitted to the mobile terminal 200 and/or the exercise equipment 100.

Figure 6:
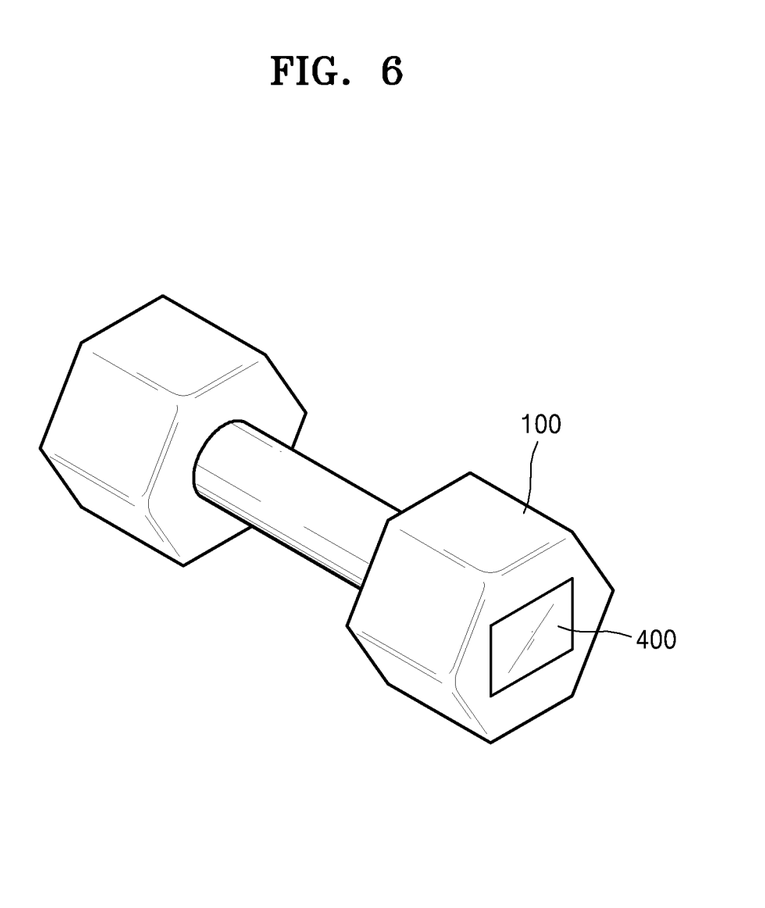
FIG. 6 illustrates exercise equipment including a display unit according to another embodiment of the inventive concept.

FIG. 6 schematically illustrates the exercise equipment 100 according to an embodiment of the inventive concept.

As illustrated in FIG. 6, the exercise equipment 100 may include a display unit 400. The form of the display unit 400 is not limited to the illustrated form, and may have any form including a screen capable of providing information to a user.

The memory of the exercise equipment 100 stores information about a predetermined posture requested at first for recognition of a user's body condition, information about the user's body condition, an exercise method, an exercise posture, and an exercise amount that are suitable for a user, and an exercise method and an exercise amount that are actually used by the user based on provided information.

The above information may be transmitted to and displayed on the mobile terminal 200 including a display for information recognition by a user. As the information is displayed on the display of the mobile terminal 200, the user may recognize the displayed information.

According to another embodiment of the inventive concept, the exercise equipment 100 may include the display unit 400, as illustrated in FIG. 6, such that the user may recognize the information through the display unit 400 of the exercise equipment 100 without separately checking the display of the mobile terminal 200.

According to the current embodiment, the user may directly check the display unit 400 provided on the exercise equipment 100, thus providing user convenience.

Figure 7:
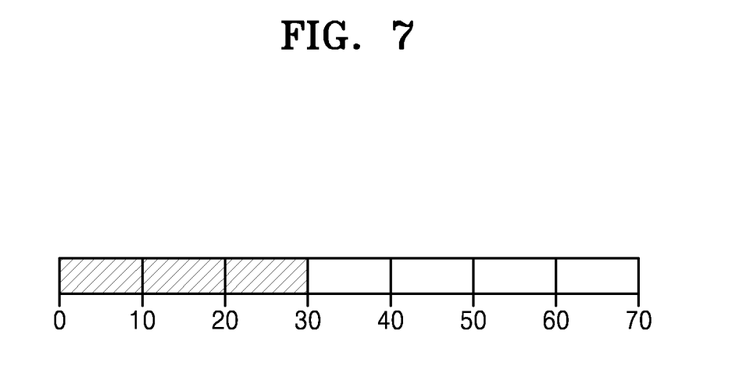
FIG. 7 illustrates a graph showing the amount of exercise of a user.

FIG. 7 illustrates a graph showing the amount of exercise of a user.

As illustrated in FIGS. 6 and 7, on the display unit 400 of the exercise equipment 100 or the display of the mobile terminal 200, a graph showing the amount of exercise done by the user may be displayed.

Although an exercise amount graph in the form of a bar graph is illustrated in FIG. 7, any form showing the amount of exercise done by the user may be possible without being limited to the form illustrated in FIG. 7.

A target exercise amount suitable for a user and the amount of exercise that the user actually does may be indicated in different colors on the same graph. In this case, the user may check the target exercise amount and the current amount of exercise the user has done. However, a way to display the target exercise amount and the current amount of exercise the user has done is not limited to this example, and any method capable of facilitating checking by the user may be possible.

Figure 8:
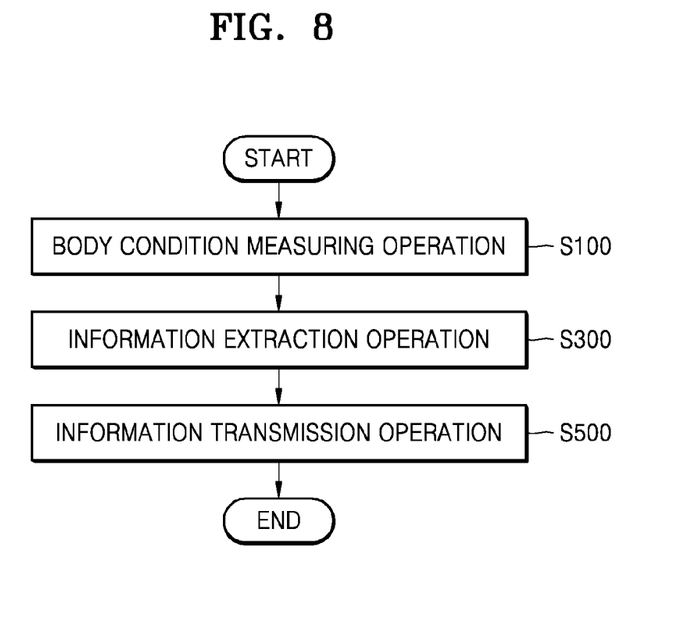
FIG. 8 is a flowchart illustrating a customized exercise method according to an embodiment of the inventive concept.

FIG. 8 is a flowchart illustrating a customized exercise method according to an embodiment of the inventive concept.

Before the user starts to exercise, a body condition measuring operation S100 may be performed in which a user's body condition is measured using a sensor included in the exercise equipment.

This operation is intended to maximize exercise efficiency of the user and to provide user convenience because suitable exercise posture, exercise method, and exercise amount differ depending on a body condition of an individual user.

A type of the sensor included in the exercise equipment and a method of recognizing various body conditions of the user using the sensor have already been described, and thus will not be described at this time for convenience.

Once the user's body condition is recognized in the body condition measuring operation S100, information about the body condition may be transmitted to the server. The server may store the information about the exercise method and the exercise amount suitable for the body condition, and so forth. Thus, once the information about the user's body condition is transmitted to the server, an information extraction operation S300 is performed in which the exercise method, the exercise amount, and so forth corresponding to the transmitted body condition may be extracted from the stored information.

Once the information about the exercise method, the exercise amount, and so forth suitable for the user is extracted from the server, an information transmission operation S500 is performed in which the information is transmitted to the mobile terminal and/or the exercise equipment of the user.

The user may exercise based on the information about the exercise method, the exercise amount, and so forth, provided through the mobile terminal including the display or provided through the exercise equipment including the display unit.

The exercise equipment may include a memory that stores information, and information that may be stored in the memory has already been described and thus will not be described repetitively for convenience.

Figure 9:
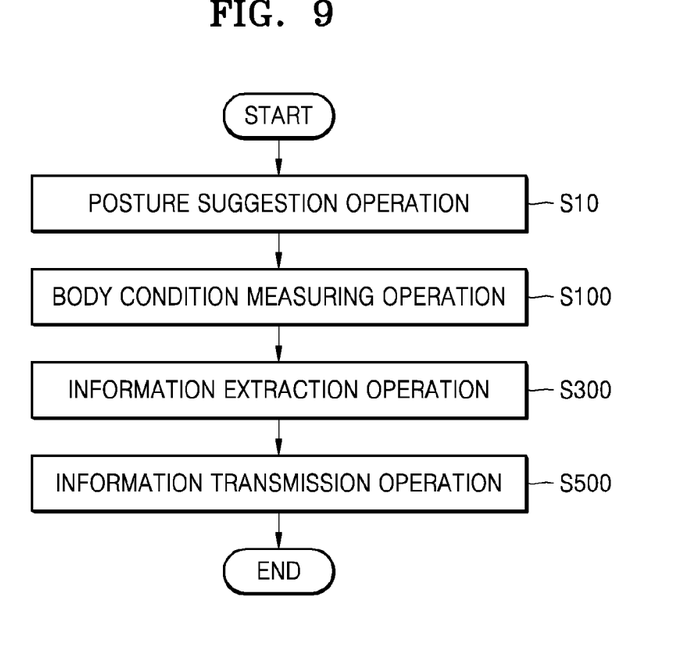
FIG. 9 is a flowchart illustrating a customized exercise method according to another embodiment of the inventive concept.

FIG. 9 is a flowchart illustrating a customized exercise method according to another embodiment of the inventive concept.

As illustrated in FIG. 9, a posture suggestion operation S10 is performed prior to the body condition measuring operation S100. As described above, to measure the user's body condition, the user may hold a requested predetermined posture.

That is, to request the user to hold the predetermined posture, the predetermined posture stored in the memory may be transmitted to the mobile terminal and displayed on the display of the mobile terminal in operation S10.

In the posture suggestion operation S10, the user holds the requested predetermined posture, and in this state, the body condition measuring operation S100 may be performed by the sensor included in the exercise equipment.

Once the suitable exercise method, exercise posture, and exercise amount are provided to the user in the information transmission operation S500, the user may exercise using the exercise equipment based on the provided exercise method, exercise posture, and exercise amount.

Figure 10:
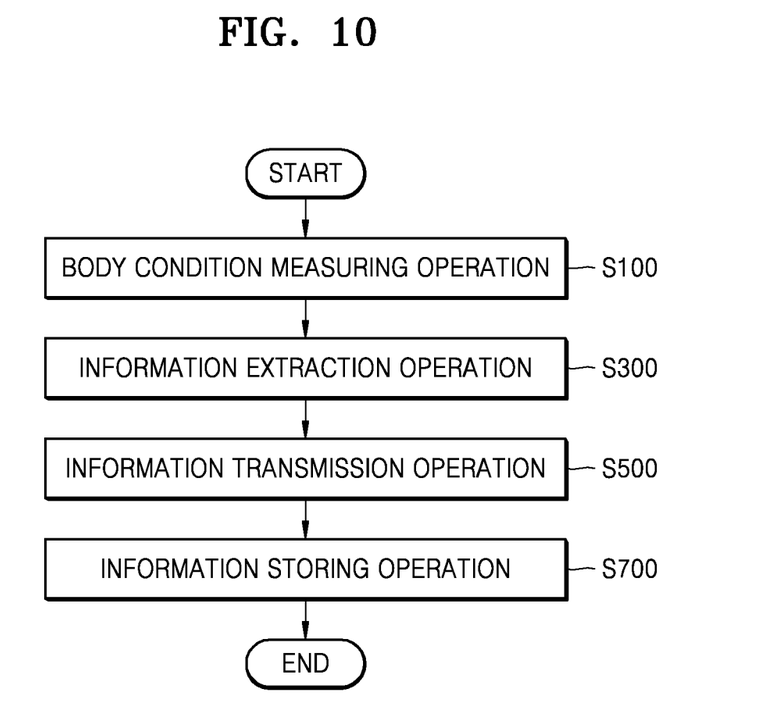
FIG. 10 is a flowchart illustrating a customized exercise method according to another embodiment of the inventive concept.

FIG. 10 is a flowchart illustrating a customized exercise method according to another embodiment of the inventive concept.

Once the user exercises, an information transmission operation S500 is performed in which information about the exercise method, the exercise amount, and so forth actually used to exercise is transmitted to the mobile terminal and/or the server and an information storing operation S700 is performed in which the transmitted information is stored.

That is, the information about the user's body condition and the information about the exercise done by the user may be stored in the mobile terminal and/or the server to provide an exercise method customized for an individual user based on the stored information.

According to an embodiment of the inventive concept, when the user exercises using exercise equipment, information about an exercise method, an exercise amount, and so forth suitable for an individual user is provided, allowing the user to exercise optimally and thus maximizing exercise efficiency.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the inventive concept as defined by the following claims.

What is claimed is:

1. A customized exercise system comprising:
a dumbbell or set of dumbbells comprising a sensor;
a server storing information about an exercise method and an exercise amount corresponding to a body condition; and
a mobile terminal receiving information about the exercise method and the exercise amount that are suitable for a user from the server and providing the transmitted information to the dumbbell or set of dumbbells,
wherein the body condition of an individual user is determined using the sensor, and the body condition of the user determined using the sensor comprises a length of an arm and a leg of the user, and wherein the length of the arm and the leg is measured as the user takes a predetermined posture while the user holds the dumbbell or set of dumbbells in hand,
wherein the dumbbell or set of dumbbells is equipment that the user can hold in both hands while exercising,
wherein is the length of the arm, the length of the arm is calculated based on a pivoting angle, time and acceleration value acquired by the sensor while the user pivots the arm while holding the dumbbell or set of dumbbells in hand,
wherein, the length of the leg is calculated based on a position acquired by the sensor while the user stands up while holding the dumbbell or set of dumbbells in hand.

2. The customized exercise system of claim 1, wherein the dumbbell or set of dumbbells comprises a memory that stores information, and the memory stores a predetermined posture required for measurement of the body condition of a user, information about the exercise method and the exercise amount that are suitable for the user, and information about an exercise amount of exercise done by the user.

3. The customized exercise system of claim 2, wherein the customized exercise system requests the user to assume the predetermined posture stored in the memory, wherein as the user holds the predetermined posture stored in the memory, the body condition of the individual user is measured by the sensor.

4. The customized exercise system of claim 3, wherein the body condition of the user, determined using the sensor, comprises a pivoting angle of the arm of the user.

5. The customized exercise system of claim 1, wherein the sensor comprises a geomagnetic sensor.

6. The customized exercise system of claim 1, wherein the sensor comprises an acceleration sensor.

7. The customized exercise system of claim 1, wherein the sensor comprises a gyro sensor.

8. The customized exercise system of claim 1, wherein the dumbbell or set of dumbbells comprises a display unit that displays information about a measured exercise amount.

9. A customized exercise method comprising:
a body condition measuring operation of measuring a body condition of a user by using a sensor included in a dumbbell or set of dumbbells;
an information extraction operation of extracting an exercise and an exercise amount that correspond to the analyzed body condition from information stored in a server; and
an information transmission operation of transmitting information about the exercise and the exercise amount that are suitable for a user from the server to a mobile terminal and/or the dumbbell or set of dumbbells of the user,
wherein the body condition of the user determined using the sensor comprises a length of an arm and a leg of the user, and wherein the length of the arm and the leg is measured as the user takes a predetermined posture while the user holds the dumbbell or set of dumbbells in hand,
wherein the dumbbell or set of dumbbells is equipment that the user can hold in both hands while exercising,
wherein, the length of the arm is calculated based on a pivoting angle, time and acceleration value acquired by the sensor while the user pivots the arm while holding the dumbbell or set of dumbbells in hand,
wherein, the length of the leg is calculated based on a position acquired by the sensor while the user stands up while holding the dumbbell or set of dumbbells in hand.

10. The customized exercise method of claim 9, wherein the dumbbell or set of dumbbells comprises a memory that stores information, and the memory stores a predetermined posture required for measurement of the body condition of a user, information about the exercise and the exercise amount that are suitable for the user, and information about an exercise amount of exercise done by the user.

11. The customized exercise method of claim 10, further comprising a posture suggestion operation of suggesting a predetermined posture stored in the memory to the mobile terminal for measurement of the body condition of a user, before performing the body condition measuring operation.

12. The customized exercise method of claim 11, wherein the body condition analyzing operation comprises analyzing the body condition of a user by using a pivoting angle and acceleration that are sensed by the sensor in the posture suggestion operation.

13. The customized exercise method of claim 9, wherein the body condition comprises a pivoting angle of the arm of the user.

14. The customized exercise method of claim 9, further comprising an information storing operation of storing information about the exercise and the exercise amount of exercise that the user actually does in a mobile terminal and/or a server, after performing the information transmission operation.

* * * * *